US006944265B2

(12) United States Patent
Warp et al.

(10) Patent No.: US 6,944,265 B2
(45) Date of Patent: Sep. 13, 2005

(54) IMAGE PASTING USING GEOMETRY MEASUREMENT AND A FLAT-PANEL DETECTOR

(75) Inventors: Richard J. Warp, Waukesha, WI (US); Vianney P. Battle, Milwaukee, WI (US); Kenneth S. Kump, Waukesha, WI (US); Stephen W. Metz, Greenfield, WI (US); Matthew A. Halsmer, Waukesha, WI (US); Renuka Uppaluri, Pewaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 306 days.

(21) Appl. No.: 10/303,672

(22) Filed: Nov. 25, 2002

(65) Prior Publication Data

US 2004/0101103 A1 May 27, 2004

(51) Int. Cl.[7] .................................................. H05G 1/64
(52) U.S. Cl. ...................... 378/98.12; 378/62; 378/116
(58) Field of Search .......................... 378/62, 98, 98.8, 378/98.11, 98.12, 115, 116; 382/130; 250/370.08, 370.09

(56) References Cited

U.S. PATENT DOCUMENTS

| 4,613,983 A | 9/1986 | Yedid et al. |
| 5,048,103 A | 9/1991 | Leclerc et al. |

(Continued)

FOREIGN PATENT DOCUMENTS

| EP | 0 919 856 A1 | 6/1999 |
| EP | 1 092 391 A1 | 4/2001 |
| WO | WO 00/36820 A2 | 6/2000 |

OTHER PUBLICATIONS

European Search Report for Application No. EP 04 25 3177, 3 pages, Oct. 7, 2004.
European Search Report for Application No. EP 04 25 3178, 3 pages, Oct. 7, 2004.
GE Medical Systems, Education: Digital X-ray, Introduction to Digital X-ray technology, available at http://www.gemedicalsystems.com/rad/xr/education/dig_xray_intro, printed on Nov. 4, 2002, 7 pages.
Wei et al., A new fully automatic method for CR image composition by white band detection and consistency rechecking, Medical Imaging 2001, Image Processing, Progress in Biomedical Optics and Imaging, Feb. 19–22, 2001, 10 pages, vol. 2, No. 27, SPIE—The International Society for Optical Engineering, Bellingham, Washington.
Geijer et al., Digital Radiography of Scoliosis with a Scanning Method: Initial Evaluation, Radiology, Feb. 2001, 11 pages, vol. 218, No. 2, The Radiological Society of North America, Inc. (RSNA), Oak Brook, IL.

*Primary Examiner*—Edward J. Glick
*Assistant Examiner*—Courtney Thomas
(74) *Attorney, Agent, or Firm*—Foley & Lardner LLP

(57) ABSTRACT

A device for use in image pasting is described. The device includes a digital x-ray detector capable of automatic digital imaging without the use of an image intensifier; the detector preferably being a flat-panel detector. Additionally, an image pasting system using a solid-state detector is described. The system can connect the detected images to a display via a network (such as a WAN, a LAN, or the internet). Further, an image geometry measurement device for use in pasting x-ray images is disclosed. The geometry measurement device helps determine the relative position of two images to be used in image pasting. This information can be used alone, or in connection with an image pasting algorithm. Still further, methods of forming composite images are disclosed using a flat-panel detector and using the geometry of the images. The disclosed devices and systems can be integrated with other digital image pasting technology.

29 Claims, 12 Drawing Sheets

U.S. PATENT DOCUMENTS

| | | |
|---|---|---|
| 5,123,056 A | 6/1992 | Wilson .................... 382/132 |
| 5,347,570 A | 9/1994 | Haaks |
| 5,463,668 A * | 10/1995 | Kagaya .................... 378/98.2 |
| 5,485,500 A | 1/1996 | Baba et al. |
| 5,600,701 A | 2/1997 | Baba et al. |
| 5,610,404 A | 3/1997 | Possin |
| 5,648,654 A | 7/1997 | Possin |
| 5,712,890 A | 1/1998 | Spivey et al. .................... 378/37 |
| 5,833,607 A | 11/1998 | Chou et al. |
| 5,844,242 A | 12/1998 | Jalink, Jr. et al. |
| 5,986,279 A | 11/1999 | Dewaele |
| 6,097,833 A * | 8/2000 | Lobregt et al. ............. 382/130 |
| 6,178,225 B1 * | 1/2001 | Zur et al. .................... 378/98.2 |
| 6,215,849 B1 | 4/2001 | Lienard et al. |
| 6,236,708 B1 | 5/2001 | Lin et al. |
| 6,252,931 B1 | 6/2001 | Aach et al. |
| 6,273,606 B1 | 8/2001 | Dewaele et al. |
| 6,282,264 B1 | 8/2001 | Smith et al. |
| 6,465,861 B1 | 10/2002 | Liu et al. |
| 2002/0081010 A1 | 6/2002 | Chang et al. ............... 382/132 |
| 2002/0118793 A1 | 8/2002 | Horbaschek ............... 378/197 |
| 2002/0159564 A1 | 10/2002 | Wang et al. |
| 2003/0031290 A1 | 2/2003 | Sugihara et al. ............. 378/15 |

\* cited by examiner

IMAGE PASTING USING GEOMETRY MEASUREMENT AND A FLAT-PANEL DETECTOR

FIELD OF THE INVENTION

The present invention relates to collecting x-ray images generated using a digital detector for use in generating a composite image from a series of individual images.

BACKGROUND OF THE INVENTION

Image pasting, or the creation of a composite image, is usually accomplished by having a system for acquiring images with a total field-of-view larger than the detector field-of-view (FOV). For applications such as full-spine imaging or long-legs imaging, the total coverage of anatomy (e.g., 60–120 cm) exceeds that of most current detectors and film-screen systems. Modifications of the current systems need to be designed to allow imaging a total coverage larger than the detector FOV. A problem with the current systems is that the digital images formed either need to be handled manually or do not give high quality images—making the pasted image less accurate.

Typical systems for image pasting use either: film-screen (FS) cassettes—either one long-film or multiple films in a large cassette; a series of stacked computed radiography (CR) plates—CR plates are also known as photostimulable phosphor (PSP) systems; or image intensifier (II) tubes.

Many FS systems have much lower image quality (IQ) than some detectors; are difficult to handle because several films must be manually placed into a cassette, and stored; have a lower dynamic range than some detectors; and cannot be post-processed, nor can they be quantitatively analyzed.

Typical CR systems tend to be difficult to handle because several PSP plates must be placed into a large, heavy, cumbersome, custom cassette; require extra time to insert and extract plates from the cassette; have a white band artifact at the region of overlap between the two plates due to attenuation; and have lower IQ than some detectors.

II systems tend to have poor IQ and introduce distortions such as pin-cushion effects. The detector can also cause representation errors during image pasting (this has been referred to as the Pisa effect, or s-distortion), have anisotropic resolution across the field (the resolution is highest in the center of the detector, but decreases toward the periphery), may be sensitive to vibrations during movement causing additional image noise called "microphonic" noise. The distortions take extra time and processing power to correct, and the system may need to take time after reaching a position before collecting an image in order to avoid some of the noise due to the vibrations. Longer processing and pauses could mean a longer exam time, which in turn may cause an increase in patient movement artifacts.

Also, images from some systems are typically not square, but rather round. With the round shape and distortion at the edges, only a small segment through the center of each image can be used for composing the pasted image (as the images move farther apart, the span of overlap decreases). Also, a larger number of images are required (15–60 images for round systems compared with 2–5 images with square systems—the largest round systems typically having a 30 to 40 cm field of view).

Image quality is important in image pasting with respect to both image noise and resolution. Systems with a lower detective quantum efficiency (DQE) cause images to exhibit high noise levels. Therefore, these systems require higher dose to image the patient in order to achieve comparable image quality. High dose is especially undesirable in pediatric cases, and especially, as in image pasting, when the subject of interest must be exposed multiple times in order to get a full image.

High resolution is desirable when viewing sharp details in orthopedic cases. For example, the spinal vertebrae endplates and iliac crest are anatomies that require high resolution images to view. Sharp detail is also important when accurately joining two images to form a pasted image. A system for use in image pasting that can deliver a higher DQE is needed.

Typical image pasting systems also include image pasting algorithms which must search large portions of an image looking for an appropriate area of overlap. Such systems do not work as efficiently as possible because there is no frame of reference which suggests a possible starting point for the overlap. A system that can provide a starting point for an image pasting algorithm to locate the overlap is desirable.

BRIEF SUMMARY OF THE INVENTION

The present invention is directed to methods and devices for use in image pasting. The present invention is also directed to a system for use in image pasting.

One embodiment of the invention includes an x-ray source and an x-ray detector capable of automatic digital imaging without the use of an image intensifier. The detector detects x-rays transmitted from the x-ray source through a subject of interest and the resulting images have a field of view. The device also includes a position change mechanism that changes a relative position between the subject of interest and the x-ray detector, and a controller that is coupled to and controls the position change mechanism to change a relative position between the x-ray detector and the subject of interest to at least a first relative position and a second relative position. Additionally, the device has another controller that controls the collection of at least a first image detected at the first relative position and a second image detected at the second relative position, the first and second images being capable of being pasted together to form a pasted image with an image field of view larger than the field of view of the individual images. This second controller is coupled to the controller of the x-ray source operation and controller of the position change. An additional embodiment includes a geometry measurement device which provides information on the geometry of the position change mechanism. Another embodiment includes using a flat-panel detector as the x-ray detector. A further embodiment includes an image storage enabling unit that enables storage of at least one image which has been collected.

A further embodiment includes an x-ray detection unit to be used with an x-ray generating unit having an x-ray source and a first controller which controls the operation of the x-ray source, a second controller which controls collection of images, and a third controller which controls changing a relative position between an x-ray detector and the subject of interest. The x-ray detection unit includes a flat panel x-ray detector, which detects x-rays transmitted from the x-ray source through a subject of interest, the detector using a field of view to collect images. The detector detects at least a first image at a first relative position and a second image at a second relative position, the first and second images being capable of being pasted together to form a pasted image with an image field of view larger than the field of view of the first and second images individually. The x-ray detection unit also includes a position change mechanism, which changes a relative position between the detector and a subject of interest to at least the first relative position and the second relative position in response to a control signal from the position change controller. In another embodiment the x-ray detection unit further includes an image storage enabling unit, which enables storage of at least one image which has been collected.

Also disclosed is a method for collecting x-ray images for image pasting using a device having an x-ray source and a flat-panel x-ray detector using a field of view. The steps in the method include obtaining a first image of a subject of interest at a first position using x-rays transmitted through the subject of interest detected by the flat panel x-ray detector; moving the detector a distance no more than a length of a field of view of the detector in a direction of the movement; obtaining a second image of the subject of interest at a second position using x-rays transmitted through the subject of interest detected by the flat panel x-ray detector; and joining the first and second images at a line of overlap to form a pasted image having an image field of view larger than the field of view of the detector.

Further, a system for creating a composite image from at least two images generated in response to x-ray radiation passing through first and second portions of human body is disclosed. The system comprises an x-ray source; a solid-state, flat-panel, x-ray detector including a first portion for converting x-rays to light, a second portion for converting light to information represented by electrons and a third portion configured to generate digital data representative of x-ray radiation based upon the information; a movement device coupled to the detector to facilitate relative movement between the detector and the human body along a straight path, such that the detector is positioned to generate first digital data representative of the first portion and positioned to generate second digital data representative of the second portion; a processor for processing the digital data to generate composite image date representative of the first and second portions of the body; a display coupled to the processor which presents a human viewable image generated based upon the image data; and a network for coupling the display to the processor. The first portion of the x-ray detector is preferably fabricated from cesium iodide, and the second portion preferably includes amorphous silicon and is preferably a photodiode/transistor array.

Another system for creating a composite image from at least two images generated in response to x-ray radiation passing through first and second portions of the body is also disclosed. The system comprises an x-ray source configured to generate x-ray radiation; a solid-state, flat-panel, x-ray detector configured to generate digital data representative of x-ray radiation; a movement device coupled to the detector to move the detector relative to the body, such that the detector is positioned to generate first digital data representative of the first portion and positioned to generate second digital data representative of the second portion; and a processor for processing the digital data to generate composite image data representative of the first and second portions of the body. The system preferably comprises a display, and the display is preferably connectable using a network, including a local area network, a wide area network, or the internet. In one embodiment, the system can generate billing information and/or other patient related information. The information may be correlated to other information relating to the patient.

Additionally, a device for use in generating composite x-ray images using a digital x-ray device is disclosed. The improvement in the device comprises a geometry measurement device which provides information on the relative geometry of at least one image. The geometry measurement device in one embodiment is a positioner. In another embodiment, the geometry measurement device is an inclinometer.

Also, a method for use with an x-ray device having an x-ray source and an x-ray detector, of determining a relative position between a first x-ray image and a second x-ray image which have been combined to form a pasted image is disclosed. The method comprises collecting a first image at a first relative position, collecting a second image at a second relative position, measuring a geometry of the first image, and using the geometry of the first image and a geometry of the second image to aid in determining the position of the first image relative to the position of the second image in the pasted image. In one embodiment, the geometry is measured by measuring the position of the detector, and in another embodiment, it is measured by measuring the position of the x-ray source. In still another embodiment, the position is measured by measuring the position of the detector relative to at least one point of reference.

BRIEF DESCRIPTION OF THE DRAWINGS

FIG. 3b shows a pasted image made by joining the four images shown in FIG. 3a;

FIG. 8b is a diagram of the operation of the flat-panel x-ray detector shown in FIG. 8a;

DETAILED DESCRIPTION OF THE PREFERRED EMBODIMENTS

Figure 1:
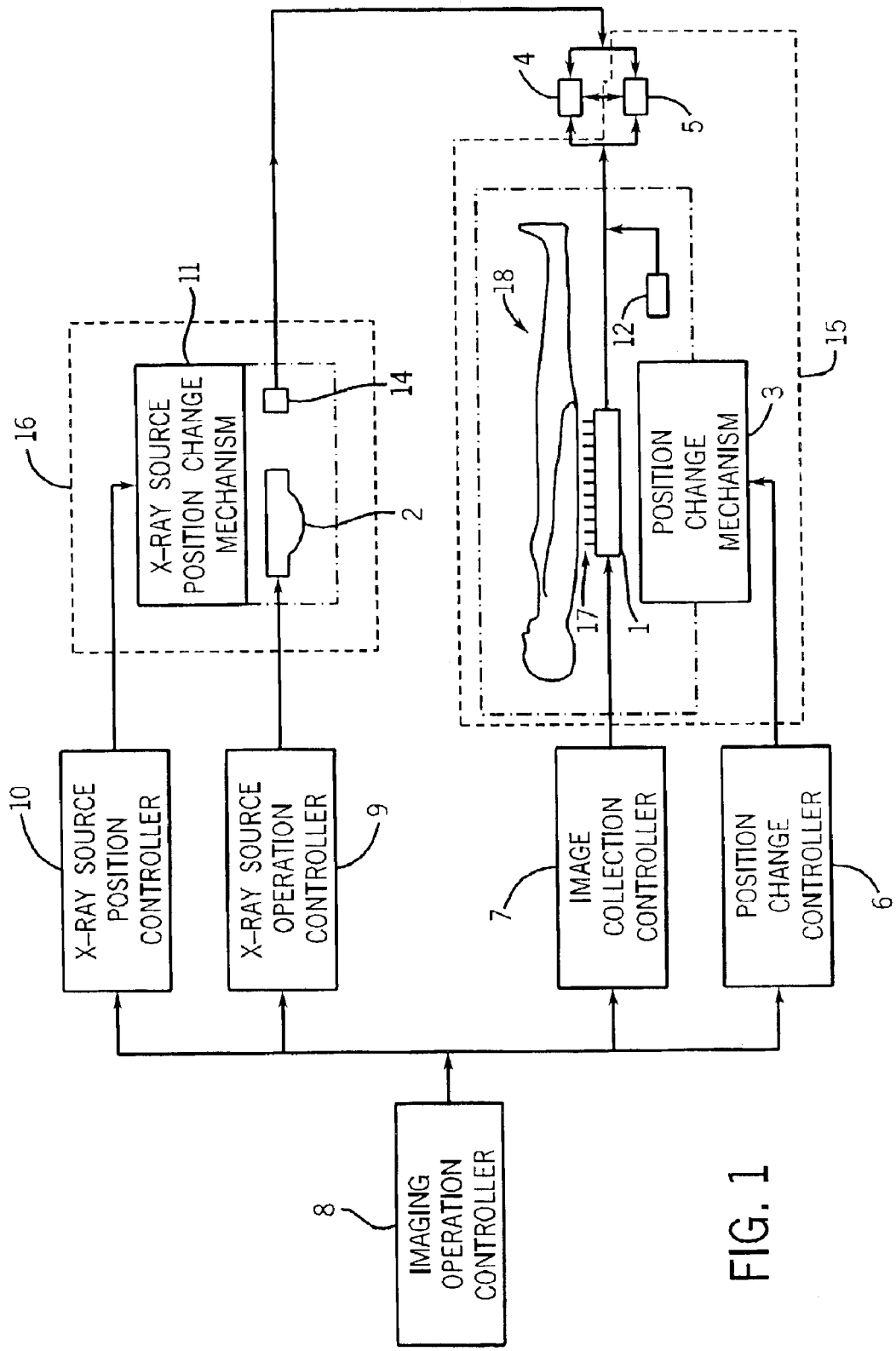
FIG. 1 is a schematic diagram showing the structure of a system for use in image pasting according to an illustrative embodiment.

FIG. 1 is a schematic diagram showing the structure of an x-ray device according to one embodiment of the present invention. The x-ray device includes components such as an x-ray detector 1, an x-ray grid 17, an x-ray source 2, a position change mechanism 3, a processor 4, an image storage enabling unit 5, a position change controller 6, an image collection controller 7, an x-ray source controller 9, an x-ray source position controller 10, an x-ray source position change mechanism 11, an imaging operation controller 8, a positioner 12, and an inclinometer 14.

The x-ray device images a subject of interest 18. The subject of interest 18 can be any number of items where taking an x-ray image of the item is desired. Some typical subjects of interest are human patients to make diagnosis, sealed packages to determine contents, and welding joints to ensure a complete weld.

In FIG. 1, the subject of interest 18 is a human patient. The patient can stand in any position, e.g., posterior-anterior (PA), anterior-posterior (AP), lateral (LAT), etc. The patient can also be in a dorsal or ventral position on a platform.

The imaging operation controller 8 controls the x-ray detector 1 to collect at least two images at two separate positions. Specifically, the imaging operation controller 8 controls the x-ray source operation controller 9 and image collection controller 7 to gather images. The imaging operation controller 8 further controls the position change controller 6 to control a change in the relative position between the x-ray detector 1 and the subject of interest 18, so that the x-ray detector 1 and subject of interest 18 are placed in at least two different relative positions.

The x-ray source operation controller 9 controls the x-ray source 2 to generate x-rays. X-rays are typically generated by having a high voltage generator generate a high voltage signal which causes an x-ray tube to emit x-rays.

The image collection controller 7 controls to collect an image at at least a first and a second position. The image collection controller 7 may control the x-ray detector 1 to detect the x-rays. Alternatively, the x-ray detector 1 may constantly be detecting images and the image collection controller 7 may control to collect only a particular image that has been detected. The image collection controller 7 may operate in many ways so long as the image collection controller 7 controls to collect an image at at least a first and a second position.

The x-rays pass through the subject of interest 18 and are detected by the x-ray detector 1. The image collected by the x-ray detector 1 may then be sent to the image storage enabling unit 5 which enables the storage of the image detected by the x-ray detector 1. The image collected by the x-ray detector 1 may alternatively be sent to the processor 4 to undergo pre-processing operations. The pre-processed image may then be sent to the image storage enabling unit 5, or be further processed.

Typically, a positioner 12 measures the geometry associated with the image by measuring the geometry of the detector and an inclinometer 14 measures the geometry associated with the image by measuring the angle of the x-ray tube. The geometry measurement devices (such as a positioner or an inclinometer) send the information to either the processor 4 or the storage enabling unit 5. The geometry measurement devices may send information on the geometry of the image along with the image, or as a separate signal or signals.

The position change controller 6 then controls the position change mechanism 3 to change a relative position between the subject of interest 18 and the x-ray detector 1. For pasting images, it is preferable (although not necessary) to have a region of overlap between two images to be joined. Also, it is easier to change the relative position between the x-ray detector and the subject of interest 18 sequentially (as opposed to skipping images and taking them at a later point in time). Thus the position change controller 6 preferably controls the position change mechanism 3 to change the relative position between the x-ray detector 1 the subject of interest 18 a distance less than the Field of View (FOV) of the detected image in the direction of movement.

The position change controller 6 may also control the position change mechanism 3 to change the relative position between the subject of interest 18 and the x-ray detector 1 a distance about equal to the Field of View (FOV) of the detected image to attempt to line the images up along the edges of the individual images. Systems which attempt to line images at their edges often end up with gaps between the images, although typically not substantial distances (i.e. usually less than 1 cm).

The relative positions set by the position change mechanism may be variable or non-variable, i.e. may have the option to move to a different position each time or may be the same each time. Additionally, some positions may be non-variable while others are variable. For instance, a starting position may be non-variable but the subsequent positions may be variable. If the positions are variable, the positions are often preset (pre-selected) before the image collection process begins. Positions may be preset using a formula that uses as inputs the starting and ending position, that then calculates the number of images to be used to cover the region from the starting to the ending position, and then calculates the optimum position for each image based on the amount of overlap.

Optionally, the x-ray source position controller 10 may control the x-ray source position change mechanism 11 to move the x-ray source 2 from one position to another position. If the x-ray source 2 changes position, it may change before, after, or at the same time as the relative position between the x-ray detector 1 and the subject of interest 18 changes.

The various controllers may be separate controllers, or all part of one control signal. For instance, in response to a single control signal the position change mechanism 3 may change the relative position between the detector and the subject of interest, and in response to the same signal, an image may be collected. Specifically, the presence of the signal may prompt movement, and the termination of the signal may indicate that an image should be collected. The various controllers involved in the system may be combined in any number of ways. Reference to the controllers individually or as a first controller, a second controller, . . . $n^{th}$ controller is not meant as an indication that the controllers are separate and distinct.

After the subsequent relative position between the subject of interest 18 and the x-ray detector 1 has been set, a subsequent image is taken in the same manner as the original image. The subsequent image may be sent to the image storage enabling unit 5, or may be sent to the processor 4 in the same manner as the original image.

The geometry measurement devices 12 and 14 also measure the geometry of the second image and send the information to either the processor 4 or the storage enabling unit 5. The geometry measurement devices 12 and 14 may send information on the geometry of the image along with the image, or as a separate signal.

More images may then be detected by repeating the operations listed above. When all the images are taken, the plurality of images may then be joined.

The x-ray detection unit 15 (including the x-ray detector 1, the x-ray position changing mechanism 3, and the storage enabling unit 5) and the x-ray generating unit 16 (including the x-ray source 2 and the x-ray source position change mechanism 11) can be manufactured and sold as two separate units. The two separate units can then be controlled to operate together by the imaging operation controller 8 (which can be part of a separate control unit, a part of the x-ray generating unit, or a part of the x-ray detection unit), after the individual units have been installed.

Figure 2:
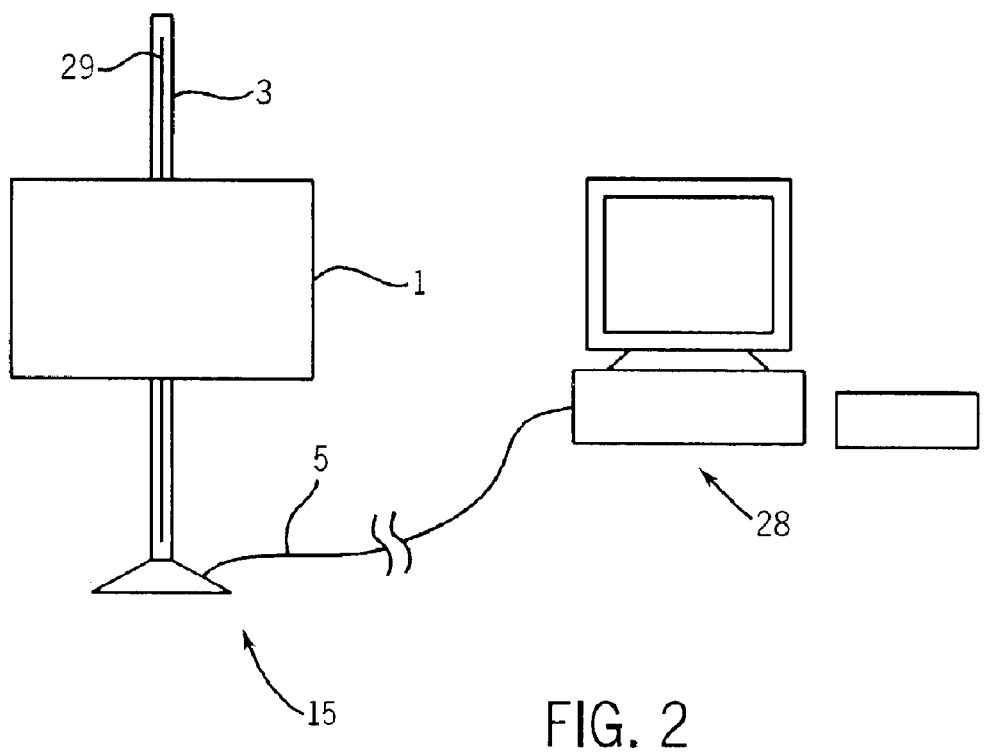
FIG. 2 is a schematic diagram showing the structure of an x-ray detection unit to be used with an x-ray generating and a set of controls according to an illustrative embodiment.

FIG. 2 shows an x-ray detection unit 15 according to one embodiment of the present invention. The x-ray detection unit 15 shown in FIG. 2 includes an x-ray detector 1, a position changing mechanism 3, and a storage enabling unit 5. The x-ray detector 1 is a flat panel x-ray detector with a rectangular field of view. The position changing mechanism 3 includes a motor which moves the detector along a track 29. The storage enabling unit is a data port connection which allows a collected image to be stored in the computer 28. The position change mechanism 3 is responsive to a position change control signal received from computer 28. The detector 1 may be responsive to an image collection control signal from computer 28 to collect images, or computer 28 may sort through the images detected by the detector 1 to determine which ones should be collected in response to an image collection control signal generated in the computer 28.

The x-ray detector 1 is preferably a 41 cm×41 cm flat-panel detector with read-out electronics 210 to acquire multiple images. Read-out electronics 210 are electronics which allow the image to be read digitally once the image is taken. Flat-panel detectors tend to have a higher image quality (IQ) than traditional image pasting systems. Higher IQ allows dose to be reduced, resolution to be increased, and/or the noise to signal ratio to be reduced. Furthermore, some flat-panel detectors can be rapidly read to acquire images in less than 150 milliseconds.

The use of a flat-panel detector for Image Pasting is also advantageous because many flat panel detectors can be used effectively at larger source to image distances (SID)—the distance from the point at which x-rays are emitted to the point at which x-rays are detected. The flat-panel systems which are effective at greater SIDs can have a SID of 170 to 240 cm, whereas typically the x-ray systems may only allow an effective SID of 80 to 150 cm. This larger SID will reduce parallax artifacts (if the "stepping" tube motion is used) and will reduce magnification of anatomies. The SID is preferably about 180 cm, but can be any distance—including less than 170 cm.

The image collected by the x-ray detector 1 will have a field of view 25 which represents the two dimensional area of the image collected. The distance of the field of view of the image in a direction of movement for a rectangular image, such as a 40 cm×40 cm image, is equal to the length of the side in the direction of movement, here 40 cm. For a circular x-ray detector 1, the distance of the field of view of the image in a direction of movement will be equal to the diameter of the image.

X-ray sources 2 generally consist of a high voltage generator which generates a high voltage signal and an x-ray tube that receives the high voltage signal and emits x-rays as a result of receiving the high voltage signal.

X-ray grids 17 are well know in the art. X-ray grids 17 can either be integrated into the x-ray detector 1, or sold as a removable unit. X-ray grids 17 remove scattered radiation from the detected image by shielding the detector from some of the x-rays that have been scattered.

The position changing mechanism 3 can be any number of mechanisms which are capable of changing the relative position between the x-ray detector 1 and the subject of interest 18. Preferably, the position changing mechanism 3 includes a motor which moves the detector in a linear motion along a vertical track. Although not preferred, the position changing mechanism 3 could be any number of other mechanisms such as a hydraulic lift which moves the detector 1, a motor which moves a platform on which the subject of interest 18 is located, etc.

The x-ray device is preferably equipped with a geometry measurement device, such as a positioner 12 or an inclinometer 14. The positioner 12 and inclinometer 14 supply geometry information to be used by a pasting algorithm to aid in determining how much two images should be overlapped by the pasting algorithm, or to determine the approximate relative position between the two images. The geometry information could conceivably, although not preferably, be used as the sole source of information to determine an amount of overlap. The positioner 12 is used to determine the relative position of a first image collected by the x-ray detector 1. The positioner 12 is preferably coupled to the x-ray detector 1. The relative positioner geometry between two images allows a pasting algorithm to better locate the point of overlap; the relative positioner geometry guides the image overlap registration allowing for more precise registration and a smaller search area. A robust image pasting algorithm should be able to accommodate small variations in positioner inaccuracy or small patient motions.

The positioner 12 may be coupled to the x-ray source 2, which positioner geometry of the x-ray source 2 gives information about the geometry of an image collected from the detector 1. This geometry information may be used by a pasting algorithm in a similar manner as the x-ray detector 1 positioner geometry information; most notably when a stepping motion (see below) is used.

The inclinometer 14 measures the amount of tilt in the x-ray source 2. The amount of tilt in the x-ray source 2 as measured by the inclinometer 14 is an indication of the relative position between the x-ray detector 1 and the subject of interest 18 for each image. The relative inclinometer 14 geometry between two images gives information about the relative geometry of an image collected from the x-ray detector 1 and thus allows a pasting algorithm to better locate the point of overlap in a similar manner as with the positioner 12 geometry.

Many geometry measurement techniques are possible with the positioner 12 and inclinometer 14. For example, a geometry measurement device can measure the amount of movement undertaken by the position change mechanism 3, the x-ray detector 1, the x-ray source position change mechanism 11, the x-ray source 2, or the subject of interest 18. Another example of possible methods of measuring position geometry for images includes measuring the distance from a designated/reference point 302 (preferably points) to a point on the position change mechanism 3, the x-ray detector 1, the x-ray source position change mechanism 11, the x-ray source 2, or the subject of interest 18 (i.e. measuring distance and/or angle of object point from the point of reference). In another example, a device may observe the position of any of the various components (such as through optics or other measuring devices). There are numerous other possible methods of measuring a relative geometry for a given collected image. Geometry information can be supplied by setting the detector to collect images at preset or non-variable positions of known geometry. This is often done as a step of measuring geometry by measuring the amount of movement to be done by one of the various components prior to actually moving the component.

Geometry measurement can be accomplished by any number of devices. Two examples of devices that are well suited for geometry measurement include a potentiometer and an encoder.

The collected images may be sent to a storage enabling unit 5. The storage enabling unit 5 can be any number of devices that enable the image data to be stored after it is collected, the exact type of device not being particularly important. The storage enabling unit 5 could be a temporary or permanent memory source integrated within the device, a removable memory source, or drive/removable medium system. The storage enabling unit 5 could also theoretically be any number of other devices that allows the data to be transferred to a separate device which separate device stores the data. Some examples of data transfer devices include a wireless transmitter and a data connection port (i.e. a USB port, serial connection port, etc.). Most preferably, the collected image unit is a data output port which allows data to be transferred to a separate unit where the image pasting occurs.

The processor 4 may perform pre-processing operations on the individual images such as correcting image fall-off or intensity normalization. This allows images to appear more even and makes for smoother transitions.

The processor 4 may also contain software that joins the collected images; the plurality of collected images can be pasted together using image pasting software. The set of images can be registered and blended together to form a final pasted image that has a FOV larger than the FOV of the individual images. The pasted image generally contains at least 40 percent of at least one image. The pasted image also generally is a two-dimensional composite image of the entire area of the subject of interest that is parallel to the detector and within the field of view of the pasted image; i.e. the image generated does not distinguish separate planes parallel to the field of view of the image. Further, the pasted image generally includes all of the structures of the subject of interest within the field of view of the pasted image minus those that do not show up using the X-ray techniques used to get the image.

Processing may also be done on the image after it has been pasted together. Some examples of such post-processing techniques include adjusting the contrast and making transitions between individual images in the pasted image appear smoother.

A number of techniques that can be used to join images are known. The techniques generally determine the relative position of one image with respect to another in a pasted image. Preferably, the technique determines the relative position based on an area of overlap, but this is not always the case. Some examples of these techniques include matching identifiable bodily structures that are in each image, using set reference points which references points are used to align the images, and overlapping the images to a point where the images are most similar in the overlapped region.

Figure 3A:
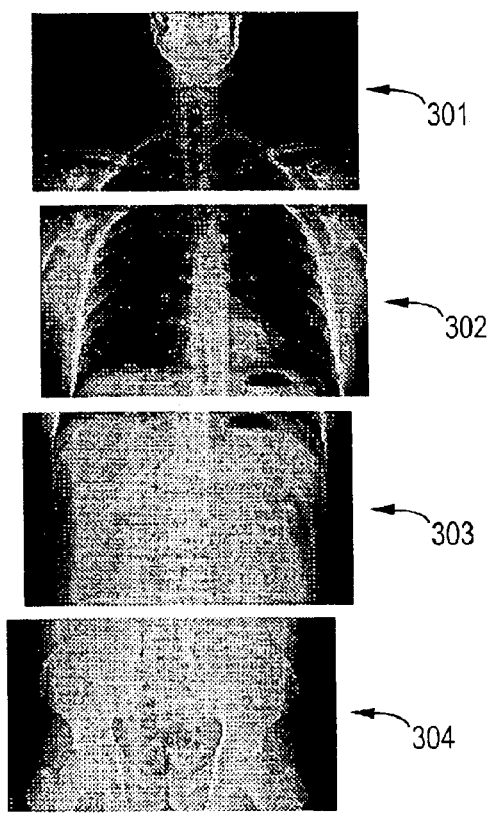
FIG. 3a shows one example of four images taken with a flat-panel x-ray detector at four different relative positions.

FIG. 3a shows a series of four individual images 301, 302, 303, 304 that have been taken with a flat-panel x-ray detector at four different relative positions.

Figure 3B:
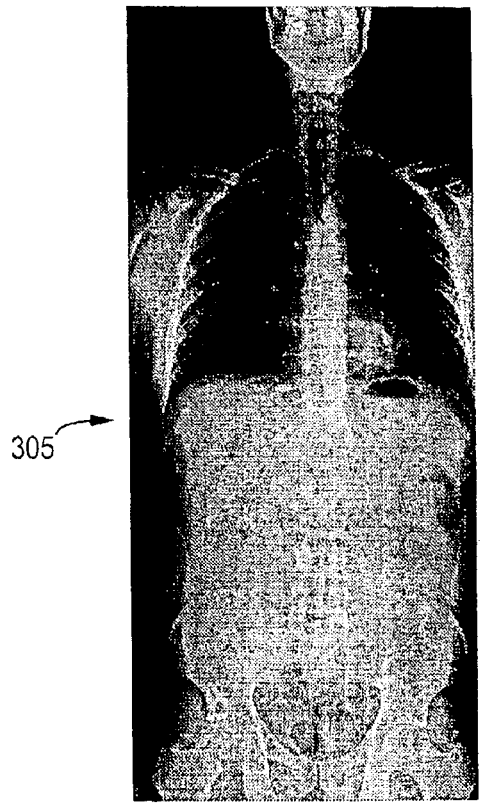

FIG. 3b shows the individual images of FIG. 3a which have been joined to form a single pasted image 305.

The pasted image can be displayed to the user. The display can also contain the original images, especially with soft-copy display. Before displaying the images to the user, whether by film or soft-copy review, the blended image dynamic range can be reduced by means of post-processing by the processor 4. Examples of post-processing methods that can be used include histogram equilization and dynamic range reduction. The pre-processing, joining, and post-processing operations can be performed by one or more processors. It should also be noted that the processing steps can be performed by a separate and distinct device which handles the images collected by the x-ray device.

Figure 4A:
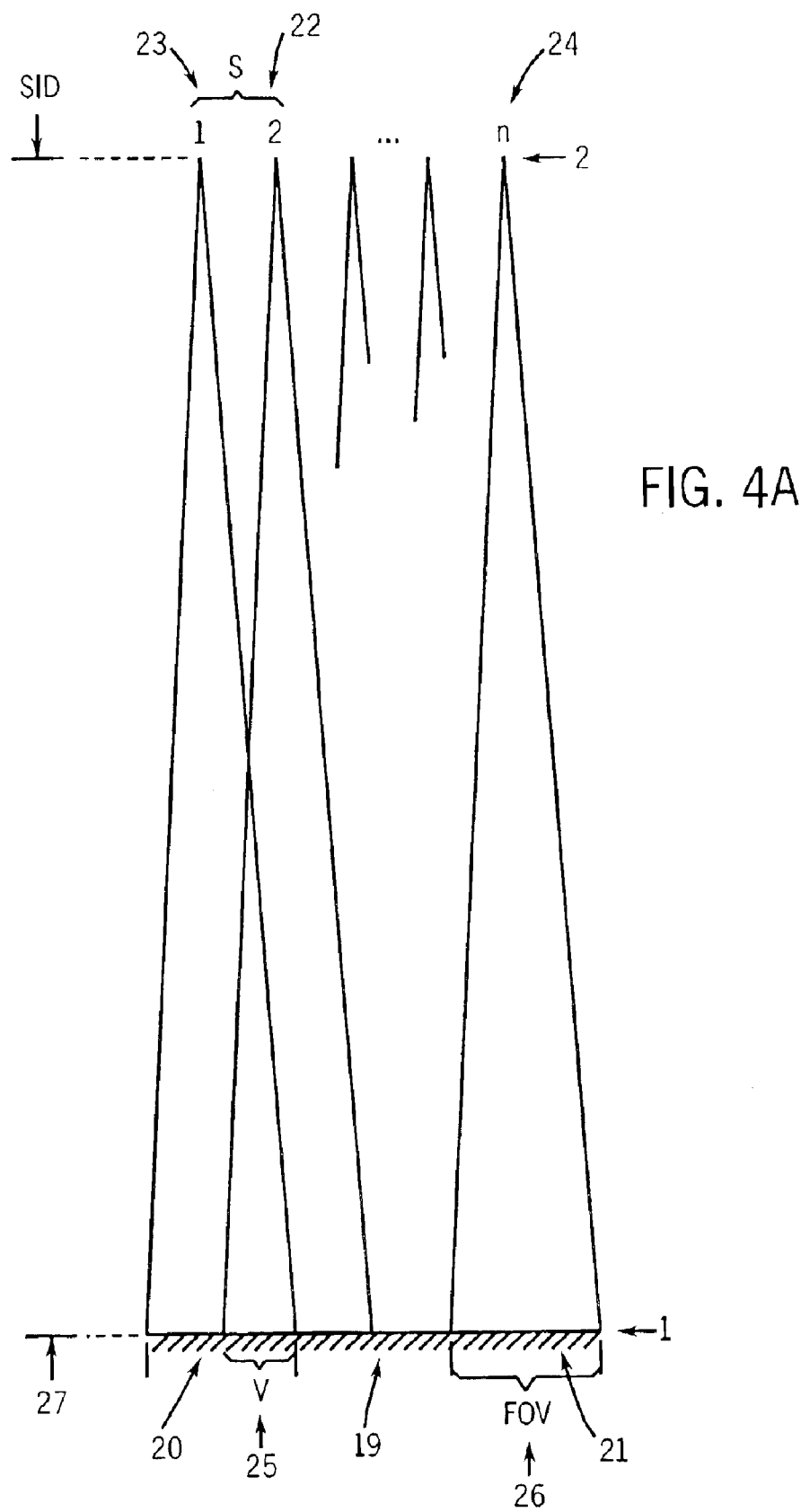
FIGS. 4a, 4b, 4c, and 4d are diagrams illustrating a few of the possible movement possibilities for the x-ray source position change mechanism and the position change mechanism.
Figure 4B:
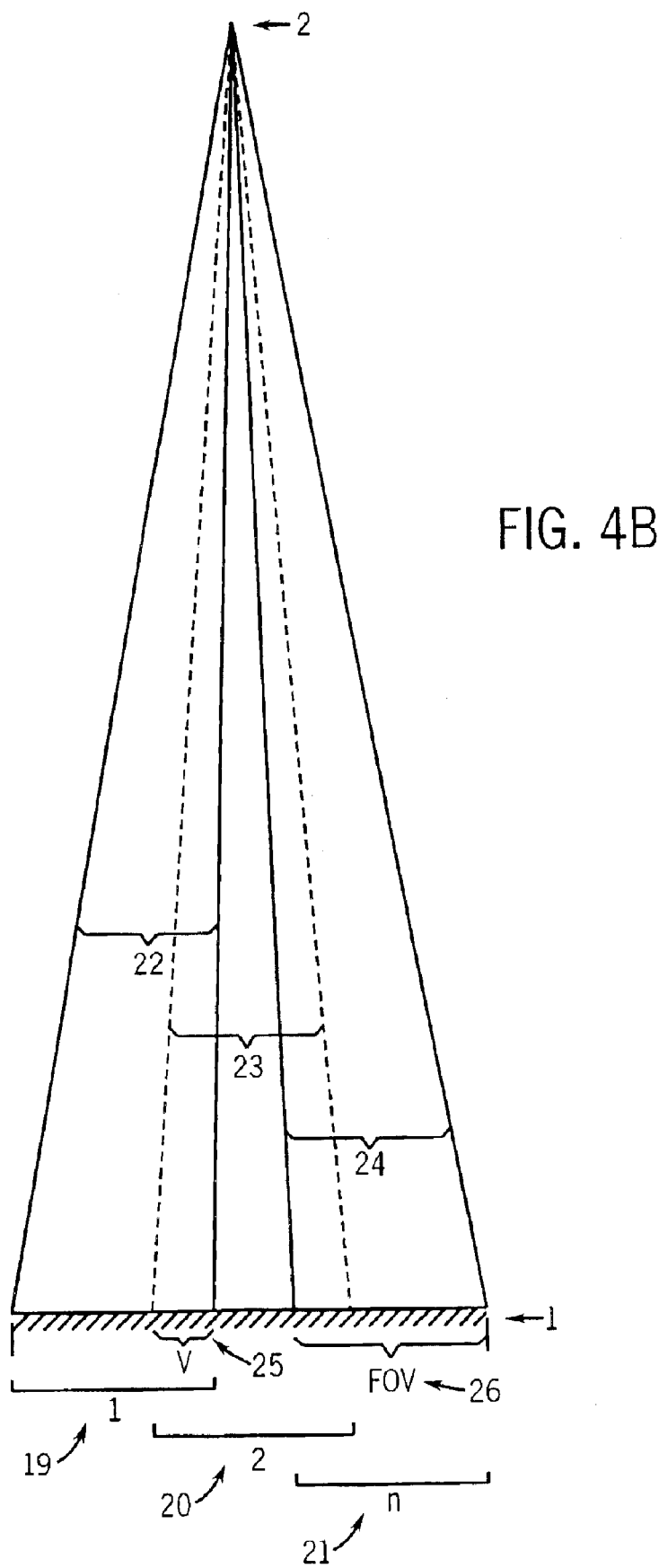

FIGS. 4a–d show some of the possible ways that a relative position can be changed between the x-ray detector 1 and the subject of interest 18 in the illustrative embodiments. As seen in FIG. 4a the x-ray detector 1 and x-ray source 2 can both be moved in parallel in a straight motion ("stepping"), or as seen in FIG. 4b the x-ray source 2 may be held stationary while it angulates ("angulating") such that multiple exposures from the tube fall centered on the detector 1. FIG. 4a shows the x-ray source 2 in a starting position 22, an intermediate position 23, and a final position 24. The positions of the x-ray source 2 correspond to the positions of the x-ray detector 1 in a starting position 19, an intermediate position 20 and a final position 21. FIG. 4a also shows the field of view 26, being used by the x-ray detector 1 in the particular image, the overlap 25 between two detected images, and the SID 27 in the illustrative embodiment shown. FIG. 4b shows the x-ray source 2 as it angulates in a starting position 22, an intermediate position 23, and a final position 24. The positions of the x-ray source 2 correspond to the positions of the x-ray detector 1 in a starting position 19, an intermediate position 20, and a final position 21.

Figure 4C:
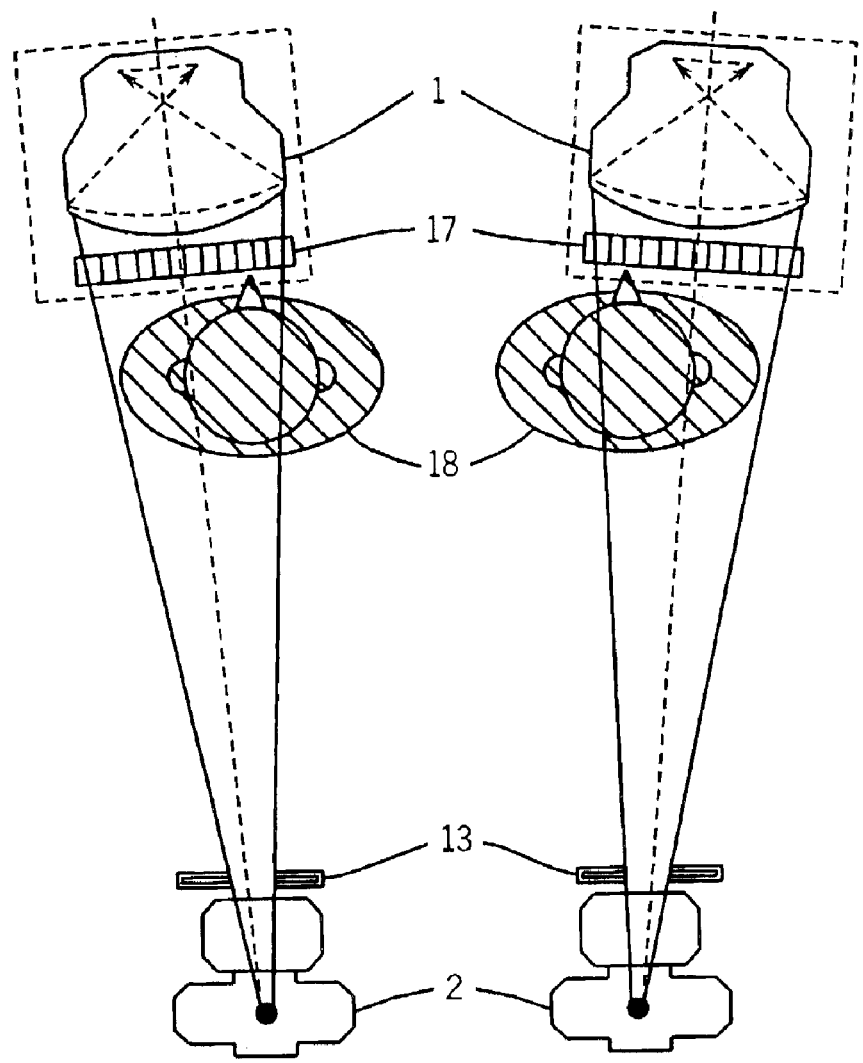
Figure 4D:
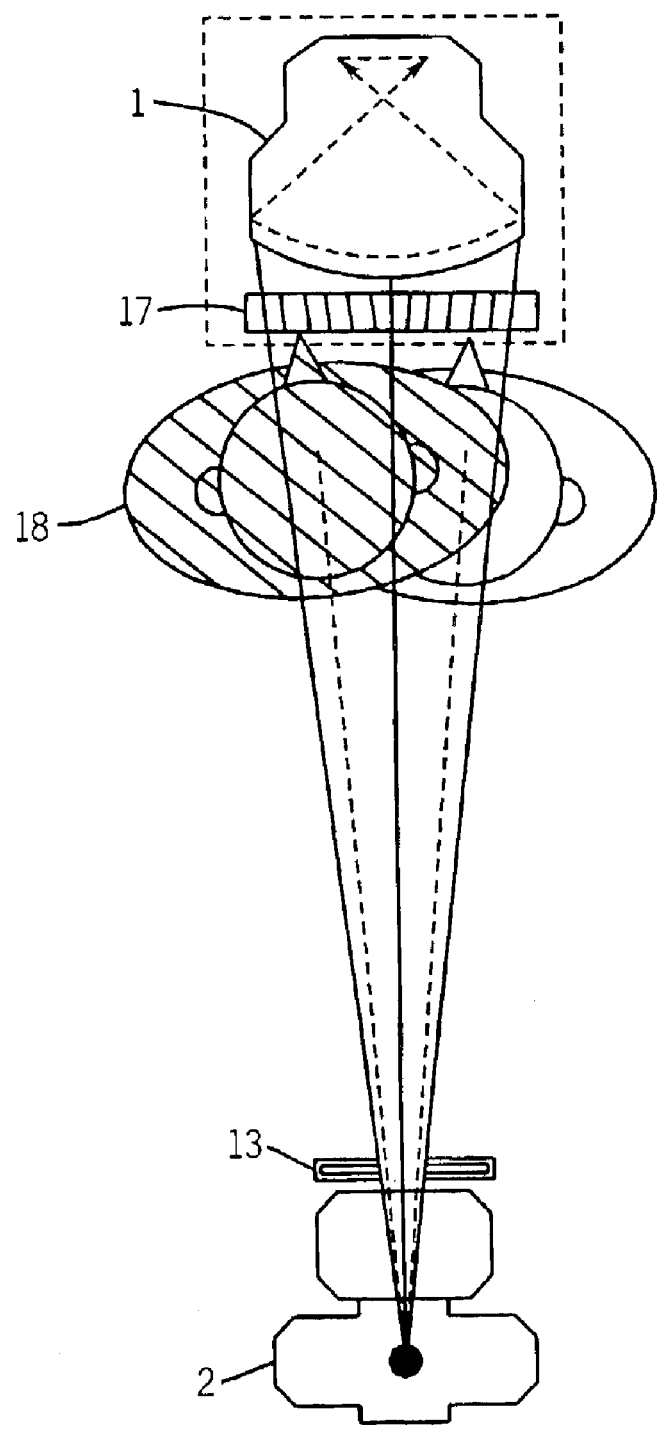

Further, as seen in FIG. 4c the x-ray source 2 may be held still while an x-ray slit 13 controls the direction of the x-rays. Alternatively, as seen in FIG. 4d the subject of interest 18 may be moved while holding the detector 1 and x-ray source 2 still. Additionally, the subject of interest 18 and x-ray source 2 may be moved while the detector 1 is held still.

It should be noted that even when the relative position between the x-ray detector 1 and the subject of interest 18 is changed by moving the subject of interest 18, the position change mechanism 3 is still functionally coupled to the x-ray detector 1, i.e. action by the position change mechanism 3 is necessary before two images can be collected from the x-ray detector 1 at two different relative positions.

While not preferable, there are other many other dynamics which the device may possess, so long as the relative position between the subject of interest 18 and x-ray detector 1 is changed. For instance, the position change mechanism 3 may move the detector 1 in a non-linear motion; one example being a circular motion between two or more spots, etc.

Of the x-ray source 2 motion possibilities, angulation will remove parallax artifacts from the pasted image. Parallax is seen in pasted images acquired with a stepping tube motion. Parallax is due to the diverging X-rays intersecting anatomies at different angles. FS and CR systems actually do not suffer from parallax because the X-ray beam is acquired in one exposure, but 11 systems affixed to C-arm gantries suffer from parallax. The clinical result of parallax is an appearance of discontinuous anatomy, or broken structures. In the chest, parallax may cause broken rib artifacts or misregistration of the spinal vertebrae. In subtraction images of the legs, parallax causes discontinuous vessels. These artifacts may distract from diagnosis or quantitative measurements.

Figure 5:
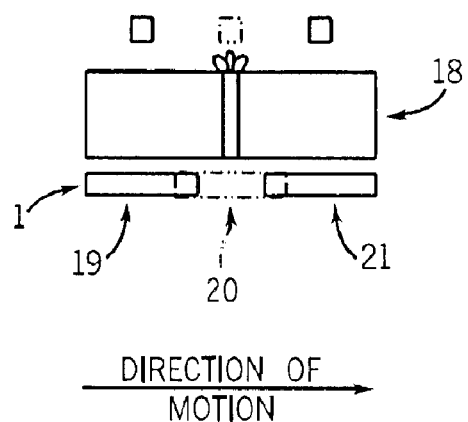
FIG. 5 is an illustration of parallel straight motion between an x-ray detector and an x-ray source.

In a preferred embodiment, to acquire the images, the x-ray detector 1 moves in a straight motion behind the subject of interest 18 parallel to the plane of the image of interest as can be seen in FIG. 5. Effort is made to minimize the air gap between the x-ray detector 1 and the subject of interest 18. In FIG. 5, the x-ray detector 1 moves in the direction of the arrow between a starting position 19, a middle position 20, and an ending position 21. At the same time, the x-ray source 2 would move in a corresponding direction and would maintain its relative position to the detector when the images are being collected.

Figure 6:
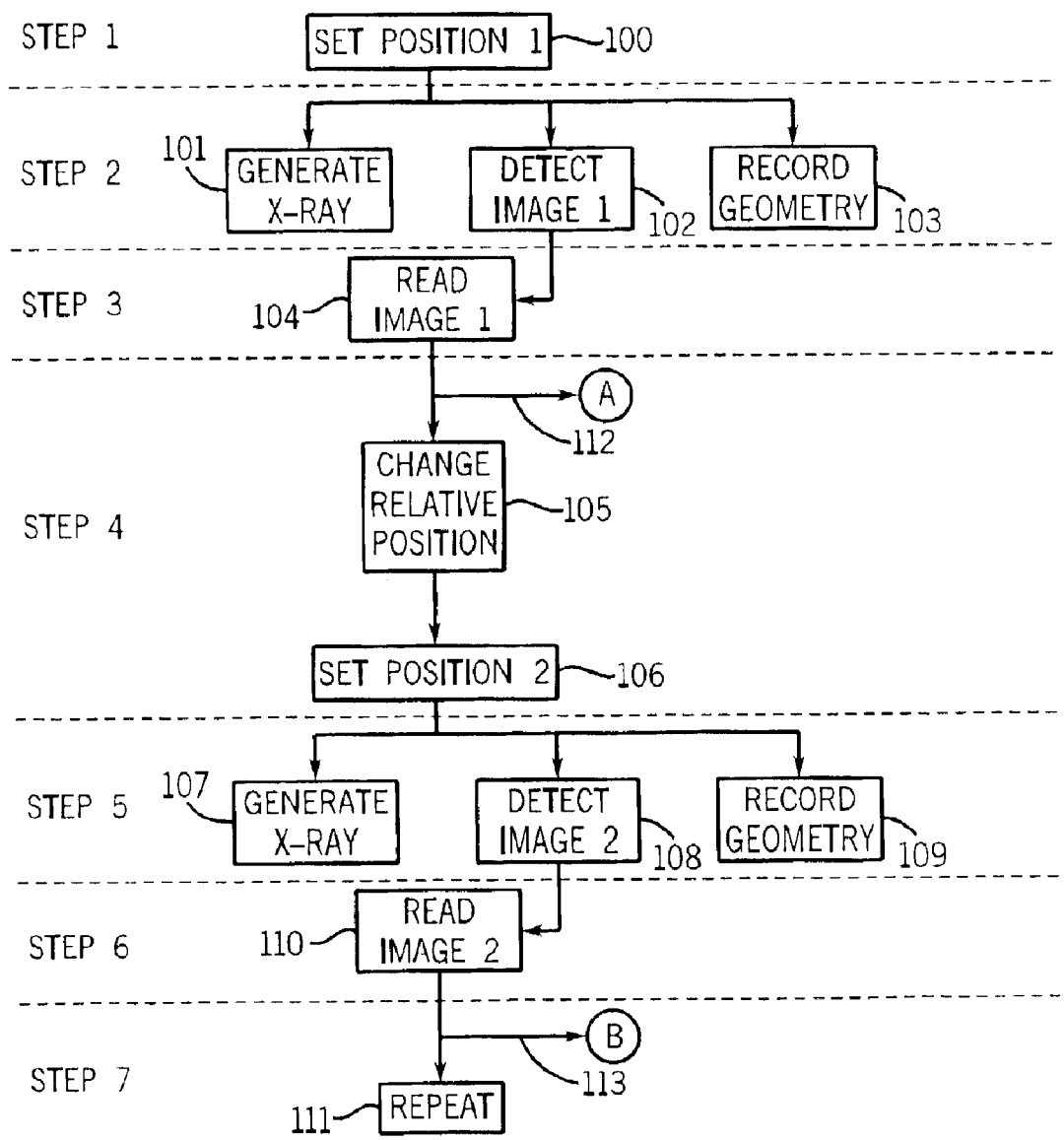
FIGS. 6 and 7 are one example of the possible timing and operation of a system for use in image pasting.
Figure 7:
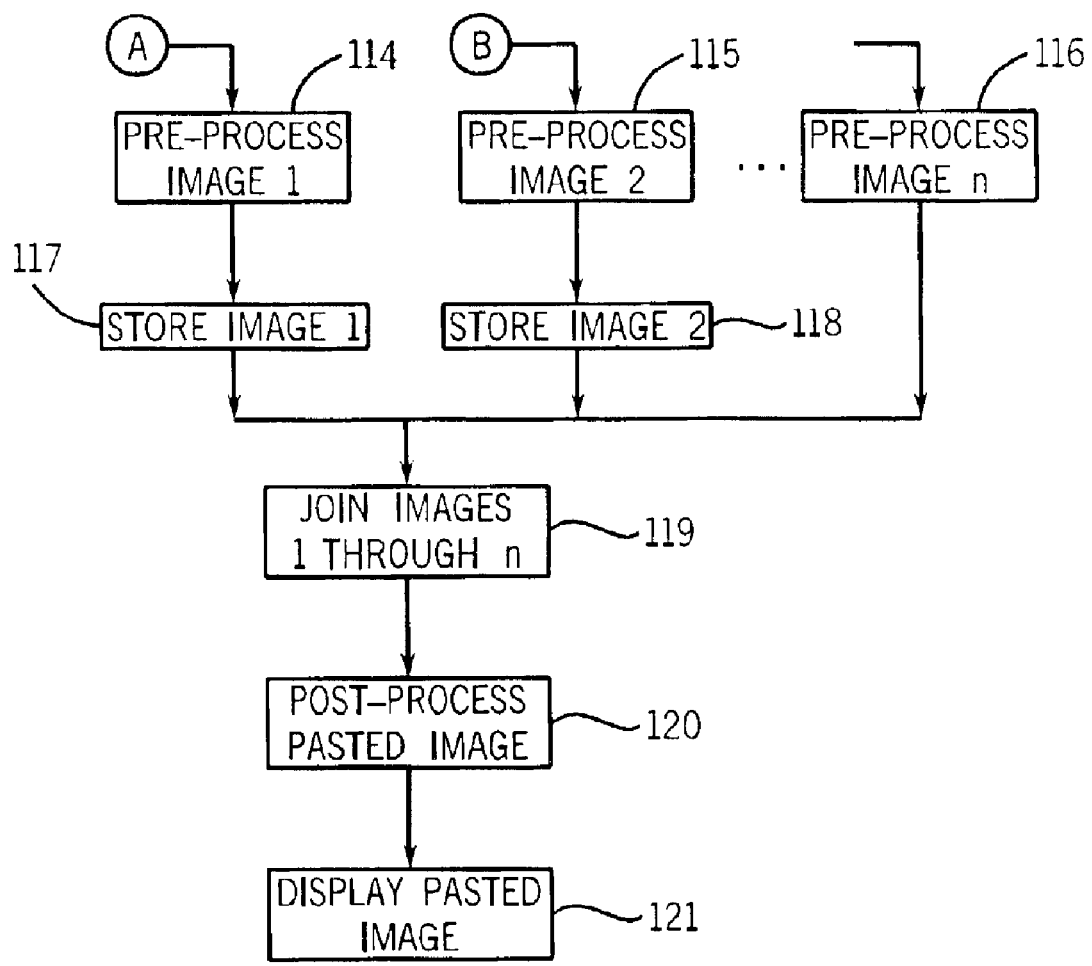

FIGS. 6 and 7 show a series of steps that can be taken which illustrate one example of how the system can function. First, an initial position is set 100. This position is typically predetermined. Once the initial position is set an x-ray is generated 101 from the x-ray source 2 and an image is detected 102 by the x-ray detector 1. The exposure duration is typically 2 ms to 2 s with 0.5 s being most typical. The geometry is also being recorded 103 by the positioner 12 and the inclinometer 14. Once the image is detected, the image is read by the x-ray detector 1 electronics. An image can typically be read in 20 to 100 ms depending on the detector. Once the image is read it is sent 112 to the processor. After the initial image is taken the position change mechanism 3 changes a relative position 105 between the x-ray detector 1 and the subject of interest 18. The subsequent position is then set 106. The x-ray detector 1 can be moved quickly without interfering with the imaging process. Typically the x-ray detector 1 is moved between two spots in about 0.5 to 10 seconds, and preferably within 2 to 6 seconds. The second position is typically predetermined. Once the subsequent position is set, the x-ray source 2 generates 107 an x-ray and the detector detects 108 an image. The geometry of the second position is also recorded 109 by the positioner 12 and inclinometer 14. The image is then read 110 by the x-ray detector 1 electronics. The image which has been read is sent 113 to the processor. If more than two images are desired, the process can be repeated 111 to gather more images.

The read images can then be pre-processed 114, 115, and 116 as mentioned earlier. The images may then be stored 117 and 118 until the images are to be joined. A processor may join at least two of the read images 119 to form a pasted image with a field of view larger than the field of view of the individual images. The pasted image may then be post-processed 120 as mentioned earlier. The post-processed image may then be displayed 121 to the user.

A further advantage of many flat panel detectors is that flat panel detectors tend to have a generally rectangular shape. When a flat panel detector is generally rectangular in shape, the full detector field of view (FOV) can be used to acquire the images. Consequently, fewer images are required to achieve the same coverage using a flat-panel detector. This reduces the total exam time which, when combined with faster imaging, ameliorates patient motion artifacts from respiratory motion, cardiac motion, bowel gas motion, diaphragm motion, etc.

Figure 8A:
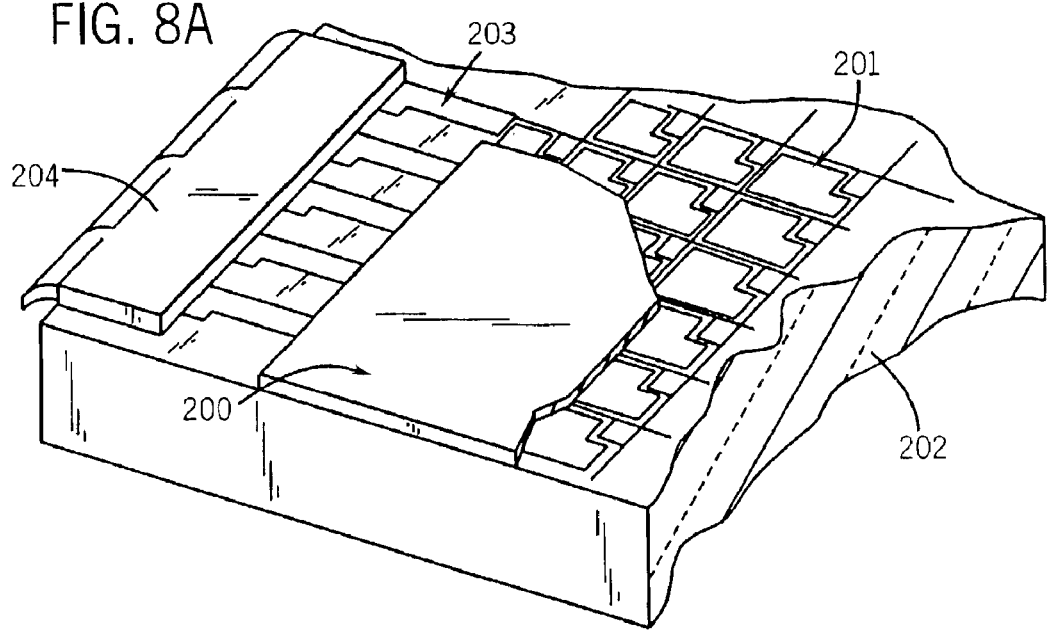
FIG. 8a is an illustration of the structure of one possible flat-panel x-ray detector.

FIG. 8a shows one example of a flat-panel x-ray detector. The flat panel detector shown in FIG. 8a includes an Amorphous Silicon Array 201 which is made of amorphous silicon diodes and thin-film transistors (TFTs). Utilizing thin film technology similar to that used in the fabrication of integrated circuits, layers of amorphous silicon and various metals and insulators are deposited on a glass substrate 202 to form an Amorphous Silicon Array 201 of photodiodes and a TFTs matrix, as well as the interconnections 203, and the contacts 204 on the edges of the panel. The scintillator 200, which converts x-ray photons into visible light photons, is made of Cesium Iodide and is deposited directly on top of the Amorphous Silicon Array 201.

Another common flat-panel detector uses a selenium array which is made of selenium diodes and thin-film transistors. The use of selenium obviates the need for a scintillator 200 because the selenium generates signals in response to the x-ray radiation directly.

Also, research is being conducted relating to polymers with properties that can be used to generate signals in response to radiation. Conceivably, these polymers, and other organic-based materials, may eventually be used to form flat panel detectors as well.

Figure 8B:
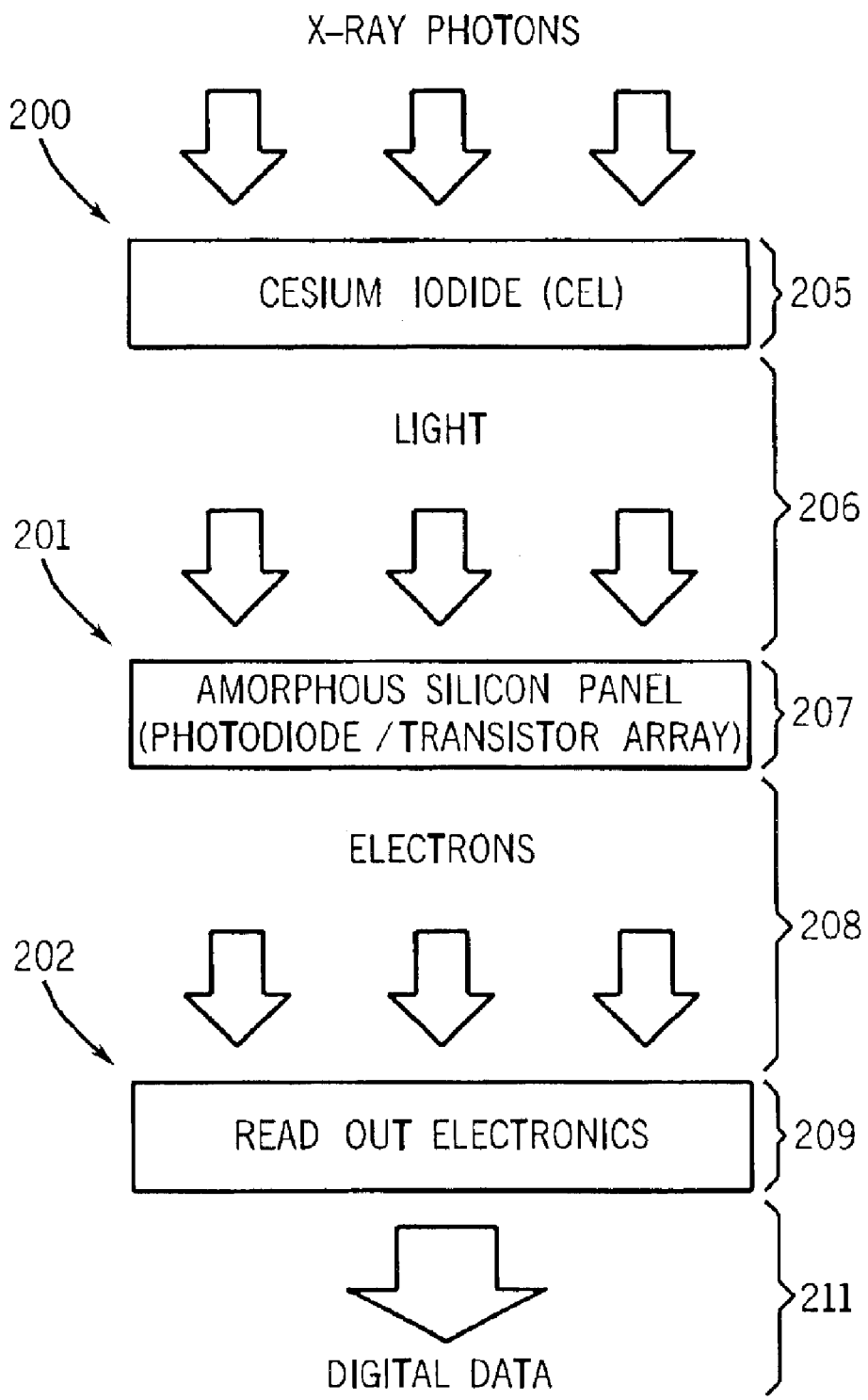

FIG. 8b shows how the flat-panel detector of FIG. 8a operates to detect signals. The cesium iodide (CsI) scintillator 200 absorbs x-ray photons, converting 205 their energy into light photons emission. This light is then channeled 206 toward the amorphous silicon photodiode array 201 where it causes the charge of each photodiode to be depleted 207 in proportion to the light it receives. Each of these photodiodes is a picture element (pixel); the spatial sampling of the image, which is the first step in image digitization, is thus performed exactly where the image is formed. The electronic charge required to recharge 208 each photodiode is then read 209 by electronics 210 and converted 211 into digital data that can then be used.

Figure 9A:
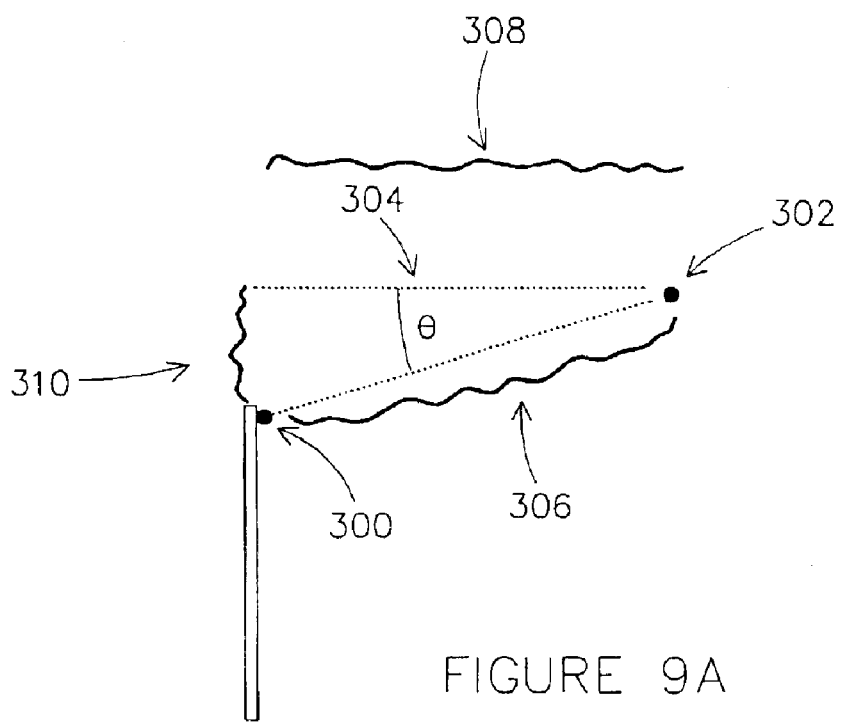
FIG. 9a is an exemplary diagram showing use of a point of reference to measure relative geometry.

FIG. 9a shows a geometry measurement device using a point of reference to measure the relative geometry of two images according to one embodiment. Reference point 302 and a point 300 on the detector 1 are used to calculate the relative geometry of an image taken by the detector. The relative distance 310 is correlated to the measured distance 306 by the equation $$\cos(\sin^{-1}(\text{shortest } 308/\text{measured } 306))*\text{measured } 306=\text{relative distance } 310.$$

The shortest distance being the distance perpendicular to the plane of the x-ray detector and going through point 300. From this, the geometry of an image can be determined in that the image extends from a relative position equal to the relative distance to a point equal to the relative distance plus the field of view of the detector.

Figure 9B:
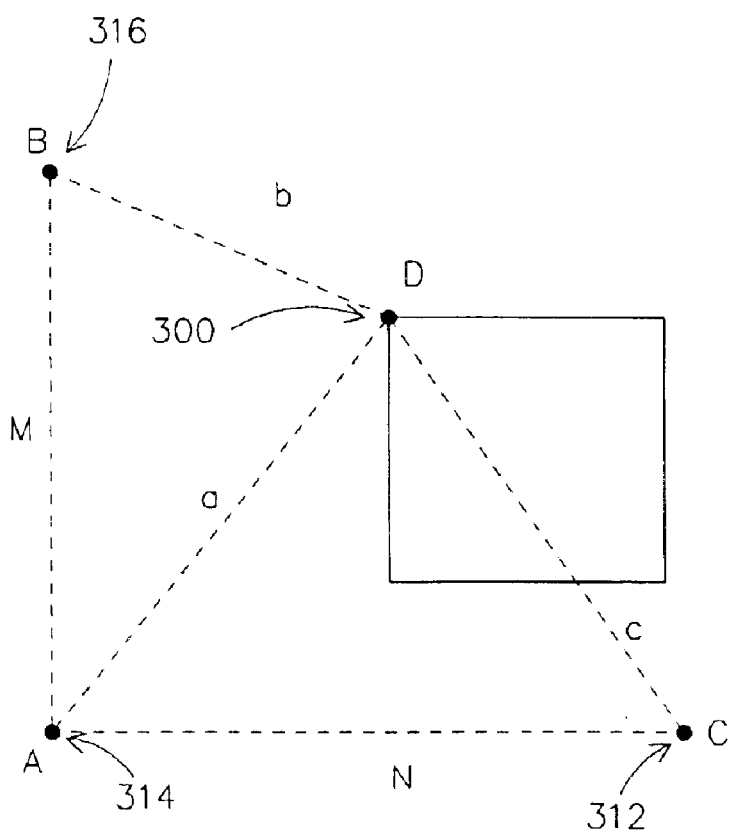
FIG. 9b is an exemplary diagram showing use of multiple points of reference to measure relative geometry.

More than one reference point can be used, especially where movement will occur in more than one direction. FIG. 9b shows one way that three reference points can be used to determine relative geometry of an image where movement occurs in a plane. Three reference points A (314), B (316), and C (312) are chosen. The angle BAC is 90° and the points A, B, and C are in the plane of the movement of the point D (300). Point A is considered the zero point, point B is at (0,M) and point C is at (N,0). Point D is at position (x,y). Distance is measured from each of the reference points to point D; giving distance AD as 'a', BD as 'b', and CD as 'c'. The following formulas tie the point (x,y) to the distances a, b, and c.

$$a^2=x^2+y^2$$

$$b^2=x^2+(M-y)^2$$

$$c^2=(N-x)^2+y^2$$

When the formulas are solved for x and y, the following values can be found:

$$y=(M^2+a^2-b^2)/2M$$

$$x=(N^2+a^2-c^2)/2N$$

If only points A and B are used, the following can be found:

$$y=(M^2+a^2-b^2)/2M$$

$$x=(a^2-(M^2+a^2-b^2)^2/4M^2)^{1/2}$$

More complicated equations to plot relative geometry using more than one reference point and/or involving movement in more than one direction can be formulated by one of ordinary skill in the art.

The data gathered by this system may potentially be compatible with current digital radiography applications. Compatibility of the data can enable integration with other advanced applications such as temporal subtraction, computer aided detection (CAD), and others that are currently used or will be developed.

Many hospitals are also becoming networked, allowing information to be accessed throughout the hospital, and even at home. The data obtained by the system can be sent across a network (for example a local area network, a wide area network, or the internet) to be processed or stored at some other location. Also, data can be processed at one location and a physician can access and/or print the information at another location across the network. This allows data to be stored in a database in the network and a physician to access the information from anywhere, including from home. This also allows a physician without an x-ray device to send patients to a location which has an x-ray and then access the data soon after it is collected; allowing response times to be faster and reducing the chance that an x-ray image will be lost. The data may also be packaged to be sent via e-mail.

Another potential integration is integrating images, information, and the billing process. An image can be taken and in response to the procedure a billing record can be created. This billing record can then be sent across a network; reducing the amount of paper work needed, and decreasing the lag time between running the procedure and generating a bill (and collecting) for the procedure. This billing record would be generally correlated to the patient and/or more specifically correlated to the images created by the system, e.g. the charge for a composite image created by the system. The composite image may be integrated with other patient information including patient history, doctor notes on the patient, the referral to get the image, etc. The composite image may also be integrated with other information sorted by physician or clinician.

Another possible integration is using certain aspects of the disclosed embodiments with other image pasting systems that allow for digital images to be formed. For instance, a geometry measurement device can be used with an image intensifier system using a CCD array.

The invention has been described with reference to various specific and illustrative embodiments and techniques. However, it should be understood that many variations and modifications may be made while remaining within the spirit and scope of the invention. Also, reference to a first position and a second position, or a first image and a second image, is not necessarily an indication of order.

What is claimed is:

1. A device for use in generating composite x-ray images having an x-ray source and a first controller for controlling the operation of the x-ray source comprising:
   a digital x-ray detector configured to detect x-rays transmitted from the x-ray source through a subject of interest without an image intensifier, the detector detecting image data for a field of view;
   a position change mechanism that changes a relative position between the subject of interest and the x-ray detector;
   a second controller coupled to the position change mechanism that controls a change in a relative position between the x-ray detector and the subject of interest to at least a first relative position and a second relative position; and
   a third controller that controls collection of at least a first image detected at the first relative position and a second image detected at the second relative position, the first and second images being capable of being pasted together to form a pasted image with an image field of view larger than the field of view of the individual images, and which third controller is coupled to the first controller and the second controller.

2. The device of claim 1, wherein the position change mechanism changes the relative position between the x-ray detector and the subject of interest by a distance greater than 70 percent of a length of the field of view of the detector in a direction of movement, but less than a distance equal to the length of the field of view of the detector in a direction of movement; and
   wherein the first image and the second image have a span of overlap at least equal to 30 cm.

3. The device of claim 2, wherein the second controller controls the position change mechanism to move the detector a distance between 84 percent and 96 percent of the length of the field of view of the detector in the direction of movement.

4. The device of claim 3, wherein the first image and the second image are pasted together.

5. The device of claim 2, wherein the source to image distance is more than 170 cm.

6. The device of claim 1, further comprising a geometry measurement device which provides information relating to a relative geometry of at least the first image.

7. The device of claim 1, wherein the x-ray detector is a flat-panel detector.

8. The device of claim 7, further comprising an image storage enabling unit.

9. The device of claim 8, wherein the image storage enabling unit is a memory in which a detected image can be stored.

10. The device of claim 7, wherein the source to image distance is about 170 cm to 240 cm.

11. The device of claim 7, further comprising a geometry measurement device which provides information relating to a relative geometry of the first image.

12. The device of claim 11, wherein the first image and the second image are pasted together.

13. The device of claim 7, further comprising an x-ray source movement mechanism configured to angulate the x-ray source to point the x-ray source towards the x-ray detector; and a fourth controller that is coupled to the x-ray source movement mechanism and the third controller to control movement of the x-ray source.

14. The device of claim 7, further comprising an x-ray source movement mechanism configured to move the x-ray source in a stepping manner; and a fourth controller that is coupled to the x-ray source movement mechanism and the third controller to control movement of the x-ray source.

15. The device of claim 14, wherein the source to image distance is between about 170 cm and about 240 cm.

16. The device of claim 7, wherein the first image and the second image have a rectangular shaped region of overlap.

17. The device of claim 7, wherein the first image and the second image are pasted together.

18. The device of claim 1, wherein the first image and the second image are pasted together.

19. The device of claim 8, wherein the image storage enabling unit is a data port which facilitates transmission of the first image to a separate device which can store an image detected by the detector.

20. The device of claim 8, wherein the image storage enabling unit facilitates transmission of image data through one of a local area network, a wide area network, and the internet.

21. A device for use in image pasting comprising:

an x-ray source, configured to generate x-rays;

a first controller that controls operation of the x-ray source;

a means for detecting an x-ray which has been transmitted from the x-ray source through a subject of interest, a means for changing a relative position between the subject of interest and the means for detecting an x-ray, a second controller, which is coupled to and controls the means for changing a relative position between the subject of interest and the means for detecting an x-ray, to change a relative position between the subject of interest and the means for detecting an x-ray to at least a first relative position and a second relative position;

a third controller that controls collection of at least a first image detected at the first relative position and a second image detected at the second relative position, the first and second images being capable of being pasted together to form a pasted image with an image field of view larger than the field of view of the first and second images individually, and which third controller is coupled to the first controller and second controller; and a means for storing data representative of an image detected by the means for detecting an x-ray.

22. The device of claim 21, further comprising a means for supplying geometry information of the first image.

23. The device of claim 21, wherein the first image and the second image are pasted together.

24. A device for use in generating composite x-ray images having an x-ray source, a first controller for controlling the operation of the x-ray source, an x-ray detector configured to detect x-rays transmitted from the x-ray source through a subject of interest, a position change mechanism that changes a relative position between the subject of interest and the x-ray detector, a second controller that is coupled to the position change mechanism to control a change in a relative position between the x-ray detector and the subject of interest to at least a first relative position and a second relative position, a third controller that controls collection of at least a first image detected at the first relative position and a second image detected at the second relative position, and which third controller is coupled to the first controller and the second controller; the improvement comprising:

a geometry measurement device which provides information on a relative geometry of at least the first image.

25. The device of claim 24, wherein the geometry measurement device is a positioner coupled to the x-ray detector.

26. The device of claim 24, wherein the geometry measurement device is an inclinometer coupled to the x-ray source.

27. The device of claim 24, wherein the geometry measurement device measures a relative position between the x-ray detector and at least one point of reference.

28. The device of claim 24, further comprising a flat-panel x-ray detector.

29. The device of claim 24, wherein the information on the relative geometry of the first image is used to paste the first image and the second image.

* * * * *